(12) United States Patent
Kosaku et al.

(10) Patent No.: US 8,216,150 B2
(45) Date of Patent: Jul. 10, 2012

(54) ULTRASOUND PROBE

(75) Inventors: Hideki Kosaku, Nasushiobara (JP);
Akinori Shigihara, Otawara (JP);
Takashi Kubota, Nasushiobara (JP);
Yutaka Oonuki, Otawara (JP)

(73) Assignees: Kabushiki Kaisha Toshiba, Tokyo (JP);
Toshiba Medical Systems Corporation,
Otawara-shi (JP)

( * ) Notice: Subject to any disclaimer, the term of this patent is extended or adjusted under 35 U.S.C. 154(b) by 358 days.

(21) Appl. No.: 12/440,379

(22) PCT Filed: Feb. 18, 2009

(86) PCT No.: PCT/JP2009/000662
§ 371 (c)(1),
(2), (4) Date: Mar. 6, 2009

(87) PCT Pub. No.: WO2009/113245
PCT Pub. Date: Sep. 17, 2009

(65) Prior Publication Data
US 2010/0179431 A1    Jul. 15, 2010

(30) Foreign Application Priority Data
Mar. 10, 2008   (JP) ................. 2008-059732

(51) Int. Cl.
*A61B 8/14* (2006.01)
*A61B 1/00* (2006.01)
(52) U.S. Cl. .............. 600/462; 600/146; 600/148

(58) Field of Classification Search .......... 600/400, 600/423, 433–435, 437, 450, 459, 462, 463, 600/466, 467, 471, 585, 101
See application file for complete search history.

(56) References Cited

U.S. PATENT DOCUMENTS

| | | | |
|---|---|---|---|
| 5,479,930 A * | 1/1996 | Gruner et al. | 600/459 |
| 7,771,416 B2 * | 8/2010 | Spivey et al. | 606/1 |
| 2002/0133078 A1 | 9/2002 | Jordfald et al. | |
| 2003/0028107 A1 | 2/2003 | Miller et al. | |
| 2003/0092994 A1 | 5/2003 | Miller et al. | |
| 2006/0241417 A1 * | 10/2006 | Edwardsen et al. | 600/433 |

FOREIGN PATENT DOCUMENTS
JP    2002 330971    11/2002
* cited by examiner

*Primary Examiner* — Tse Chen
*Assistant Examiner* — Patricia Park
(74) *Attorney, Agent, or Firm* — Oblon, Spivak, McClelland, Maier & Neustadt, L.L.P.

(57) ABSTRACT

The present invention provides an ultrasound probe in which bend of a tip part is fixed only in a state that it is not bent in a direction orthogonal to a direction in which ultrasonic waves are emitted from an ultrasound generation source. To be specific, the ultrasound probe includes: a rod-like tip part inserted into a body cavity; an ultrasound emitting part placed at the tip part to emit ultrasonic waves to a subject; a first bending part for bending the tip part in a direction substantially orthogonal to the emission direction; and a fixing part configured to, when the first bending part is not bending the tip part toward any side of the direction orthogonal to the emission direction, lock a rotation member of the first bending part and inhibit the first bending part from bending the tip part in the direction substantially orthogonal to the emission direction.

10 Claims, 12 Drawing Sheets

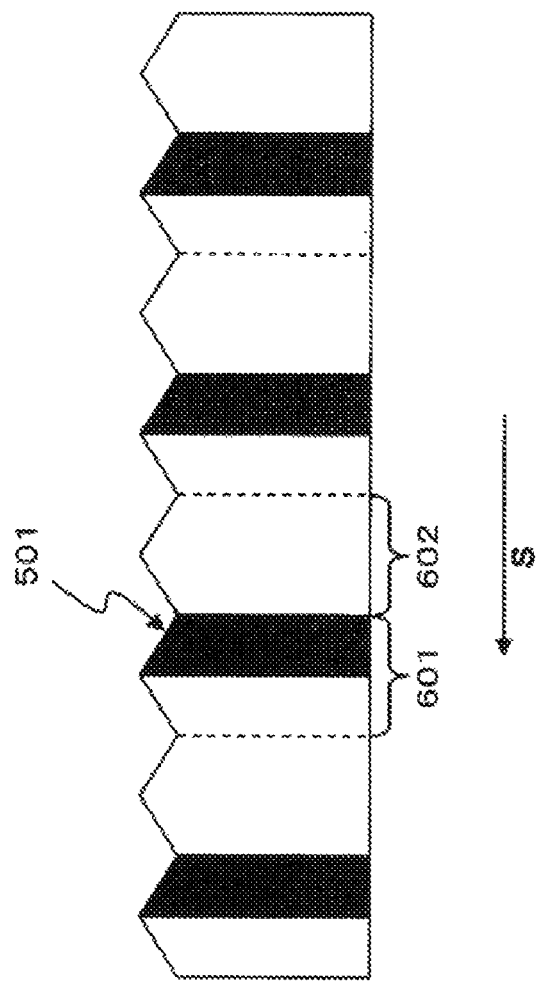
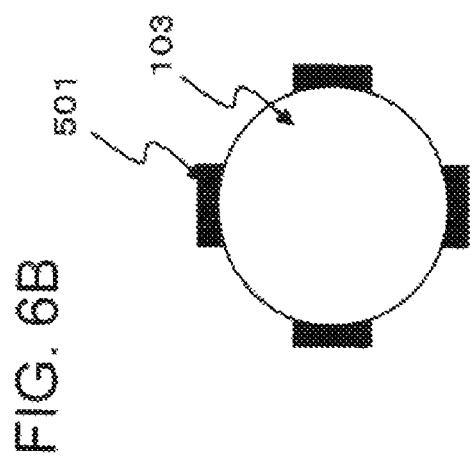
FIG. 6A
FIG. 6B

ULTRASOUND PROBE

TECHNICAL FIELD

The present invention relates to an ultrasound probe in an ultrasonic diagnosis apparatus. More specifically, the present invention relates to an ultrasound probe inserted through the mouth to emit ultrasonic waves from inside the esophagus or the stomach to the heart.

BACKGROUND ART

An ultrasonic diagnosis apparatus is equipped with an ultrasound probe that emits ultrasonic waves toward a subject by oscillating an oscillator and receives the ultrasonic waves reflected by the subject (referred to as an "ultrasound echo" hereinafter) with the oscillator. A certain type of ultrasound probe is inserted through the mouth to emit ultrasonic waves from inside the esophagus or the stomach to the heart and acquire an ultrasound echo for generating an ultrasonic image of the aorta and the tissue therearound. Such an ultrasound probe may be referred to as a "transesophageal probe" hereinafter. An ultrasonic diagnosis method using such an ultrasound probe is referred to as transesophageal echocardiography (TEE). The transesophageal probe has an ultrasound transducer serving as an ultrasound generation source, on one side of a part inserted into the subject. Ultrasonic waves are emitted from the ultrasound generation source to a target site to be observed (simply referred to as a "target site" hereinafter).

An operator like a doctor (simply referred to as an "operator" hereinafter") needs to change the direction of the ultrasound generation source of the transesophageal probe so that the transesophageal probe easily passes through the throat or the esophagus when inserted.

Moreover, the operator needs to change the direction of the ultrasound generation source of the esophageal probe so that the ultrasound generation source emits ultrasonic waves toward the target site after inserted. Therefore, the esophageal probe has a structure that can bend the tip part of the inserted part back and forth as well as right and left. Here, bending forth means bending the tip part in a direction that ultrasonic waves are emitted from the ultrasound generation source.

Bending back means bending the tip part in a direction opposite to the direction that the ultrasonic waves are emitted from the ultrasound generation source. Bending right and left is bending the tip part in a direction orthogonal to the direction that the ultrasonic waves are emitted from the ultrasound generation source. It is possible to independently execute the bending operation back and forth as well as right and left, respectively, by using a knob disposed to an operation part for operating the esophageal probe. In this structure, when the knob is rotated, a wire placed inside the inserted part is pulled and the tip part is bent in a bending structure part disposed near the tip part.

Besides, such an esophageal probe is proposed that has a mechanism for locking the bend independently or conjunctionally in the respective bending directions (e.g., refer to Patent Document 1).

Patent Document 1
Japanese Unexamined Patent Application Publication JP-A 7-250836

DISCLOSURE OF THE INVENTION

Problem that the Invention is to Solve

However, in the case of using the esophageal probe, it is impossible to visually check the tip position when the tip part is inserted in the subject. Therefore, in the case of using the ultrasound probe having the mechanism for locking the bending part as shown in Patent Document 1, when the tip part is fixed while being bent back and forth as well as right and left, the operator may insert or remove the esophageal probe without noticing that the tip part is locked in the bent state. In this case, there is a fear that the bent tip part damages an insertion path. Since an esophageal probe without the mechanism for locking the bending part will not be locked in the bent state, there is no risk that the bent tip part damages the insertion path. However, the esophageal probe without the locking mechanism may unintentionally bend back and forth as well as right and left when inserted, which may make it hard to insert the probe.

The present invention is made in view of these circumstances, and an object of the present invention is to provide an ultrasound probe in which, only in a state that a tip part is not bent in a direction orthogonal to a direction that ultrasound waves are emitted from an ultrasound generation source, the tip part can be fixed in that state.

Means for Solving the Problem

In order to achieve the above object, an ultrasound probe according to Claim 1 includes a tip part, an ultrasound emitting part, a first bending part and a fixing part as described below. The tip part is a rod-like member inserted into the body cavity. The ultrasound emitting part is placed on the tip part to emit ultrasonic waves toward a subject.

The first bending part bends the tip part in a direction substantially orthogonal to the emission direction. In a state that the first bending part is not bending the tip part in the direction orthogonal to the emission direction, the fixing part locks the first bending part to inhibit the first bending part from bending the tip part in the direction substantially orthogonal to the emission direction.

Effect of the Invention

The ultrasound probe according to Claim 1 can lock the first bending part to inhibit the first bending part from bending rightward and leftward only in a state that the tip part is not bent rightward or leftward. Thus, even if the tip part of the ultrasound probe inserted into the subject is inserted or removed in a state that the tip part of the ultrasound probe cannot be seen, it is possible to reduce the risk of damaging the insertion path, i.e., the body cavity of the subject.

Further, since it is possible to lock in a back-and-forth direction of the tip part in a state that the ultrasound generation source faces the target site, it is possible to accurately emit ultrasonic waves to the target site.

BRIEF DESCRIPTION OF THE DRAWINGS

FIG. 6A is a developed view of the periphery of the second rotation member according to the first embodiment.

FIG. 6B is a plan view of the second rotation member according to the first embodiment taken from the pressing member side.

DESCRIPTION OF REFERENCE NUMERALS AND SYMBOLS

Figure 1:
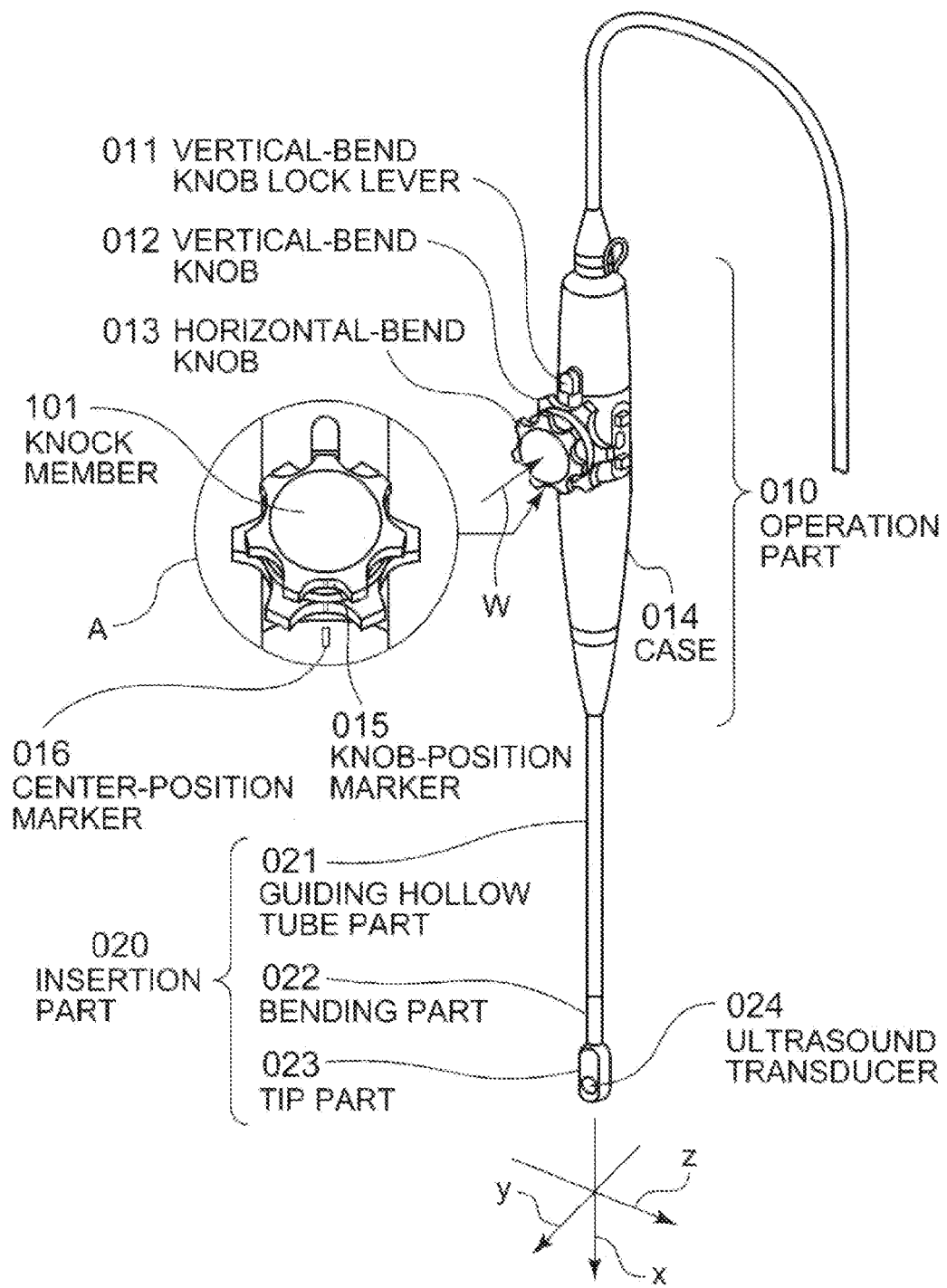
FIG. 1 is a perspective view of an ultrasound probe according to the present invention.

010: operation part
011: vertical-bend knob lock lever
012: vertical-bend knob
013: horizontal-bend knob
014: case
015: knob-position marker
016: center-position marker
020: insertion part
021: guiding hollow tube part
022: bending part
023: tip part
024: ultrasound transducer
100: fixing part
101: knock member
102: holder member
103: pressing member
104: second rotation member
105: axial tube member
106: first elastic member
110: fixing member
111: holding member
112: convex
113: second elastic member
201: rotation member
202: concave
401: support column

BEST MODE FOR CARRYING OUT THE INVENTION

First Embodiment (Entire Configuration)

First, the entire configuration of an ultrasound probe according to an embodiment will be described with reference to FIG. 1. FIG. 1 is a perspective view of the ultrasound probe according to this embodiment.

The ultrasound probe according to this embodiment includes an operation part 010 and an insertion part 020, which are shown in FIG. 1, and also includes a not-shown connector part. Section A circled in FIG. 1 is a magnified view showing a vertical-bend knob lock lever 011, a vertical-bend knob 012 and a horizontal-bend knob 013 taken from an arrow W direction.

The insertion part 020 is a part inserted into the body of the subject. The insertion part 020 includes a guiding hollow tube part 021, a bending part 022, and a tip part 023.

The guiding hollow tube part 021 is composed of a soft member.

Moreover, the guiding hollow tube part 021 is hollow. In the hollow of the guiding hollow tube part 021 is incorporated a cable for connecting a transceiver (not shown) of an ultrasound diagnosis apparatus main body (not shown) and an ultrasound transducer 024 to transmit electric signals. Moreover, four wires for tilting the tip part 023, which will be described later, are passed through the hollow of the guiding hollow tube part 021.

The ultrasound transducer 024 is placed on the tip part 023. This ultrasound transducer 024 is equivalent to an "ultrasound emitting part" in the present invention. The ultrasound transducer 024 converts pulse signals transmitted from the transceiver disposed to the ultrasound diagnosis apparatus main body into ultrasonic waves, and emits the ultrasonic waves toward a site to be examined of the subject (simply refer to as a "target site" hereinafter). Further, the ultrasound transducer 024 receives the ultrasonic waves reflected by the subject (refer to as an "ultrasound echo" hereinafter) to convert the ultrasound echo into electric signals for forming an ultrasonic image and output the electric signals to the aforementioned transceiver. Further, the four wires passed through the guiding hollow tube part 021 and bending part 022 are connected to the tip part 023. The four wires are fixed to the tip part 023, respectively, at an end in an emission direction of ultrasonic waves from the ultrasound transducer 024, an end in a direction opposite to the emission direction of the ultrasonic waves, and both side ends in a direction orthogonal to the emission direction of the ultrasonic waves. For convenience of description, a direction from the operation part 010 to the insertion part 020, i.e., an arrow X direction will be referred to as a "downward direction" hereinafter. Moreover, a direction from the insertion part 020 to the operation part 010, i.e., a direction opposite to the arrow X direction will be referred to as an "upward direction." Moreover, an emission direction of ultrasonic waves from the ultrasound transducer 024, i.e., an arrow Y direction shown in FIG. 1 will be referred to as a "forward direction." Moreover, a direction opposite to the emission direction of the ultrasonic waves, i.e., a direction opposite to the arrow Y direction will be referred to as a "backward direction." Moreover, of directions orthogonal to the emission direction of ultrasonic waves, an arrow Z direction will be referred to as a "rightward direction," and a direction opposite to the arrow Z direction will be referred to as a "leftward direction." In other words, the four wires are fixed to the "forward" end, "backward" end, "rightward" end and "leftward" end of the tip part 023, respectively.

The bending part 022 is composed of a softer material than the guiding hollow tube part 021. When the wires are pulled and a force is applied from the wires in one of the forward, backward, rightward and leftward directions of the tip part 023, the bending part 022 is bent in the direction of application of the force. Bending of the bending part 022 tilts the tip part 023 in the bending direction.

The operation part 010 is a part to control the tilt of the tip part 023 inserted into the body of the subject. The operation part 010 includes the vertical-bend knob lock lever 011, the vertical-bend knob 012, the horizontal-bend knob 013, and a case 014. The vertical-bend knob 012 and the wires are equivalent to a "second bending part" in the present invention, and the horizontal-bend knob 013 and the wires are equivalent to a "first bending part" in the present invention.

The vertical-bend knob 012 is attached to the case 014 of the ultrasound probe so as to be capable of rotating. Further, a rotatable disk is disposed to the center axis of the vertical-bend knob 012. As described above, the wires connected to the disk rotated by the vertical-bend knob 012 and the wires connected to a disk rotated by the horizontal-bend knob 013 form an angle of 90 degrees (not shown).

When the operator rotates the vertical-bend knob 012, the disk rotates in response. The wire fixed to the forward end of the tip part 023 and passed through the bending part 022 and the guiding hollow tube part 021 is connected to the rightward end of the disk of the vertical-bend knob 012. The wire fixed to the backward end of the tip part 023 and passed through the bending part 022 and the guiding hollow tube part 021 is connected to the leftward end of the disk of the vertical-bend knob 012. When the vertical-bend knob 012 is rotated clockwise when viewed from the arrow W direction, the wire connected to the left side of the disk is pulled, the bending part 022 bends forward, and the tip part 023 tilts backward. When the vertical-bend knob 012 is rotated counterclockwise when viewed from the arrow W direction, the wire connected to the right side is pulled, the bending part 022 bends backward, and the tip part 023 tilts backward.

The horizontal-bend knob 013 is attached to the case 014 of the ultrasound probe so as to be capable of rotating. Further, a rotatable disk is disposed to the horizontal-bend knob 013. When the operator rotates the horizontal-bend knob 013, the disk rotates in response. The wire fixed to the rightward end of the tip part 023 and passed through the bending part 022 and the guiding hollow tube part 021 is connected to the rightward end of the disk of the horizontal-bend knob 013. The wire fixed to the leftward end of the tip part 023 and passed through the bending part 022 and the guiding hollow tube part 021 is connected to the leftward end of the disk of the horizontal-bend knob 013. When the horizontal-bend knob 013 is rotated clockwise when viewed from the arrow W direction, the wire connected to the left side is pulled, the bending part 022 bends leftward, and the tip part 023 tilts leftward.

When the horizontal-bend knob 013 is rotated counterclockwise when viewed from the arrow W direction, the wire connected to the right side is pulled, the bending part 022 bends rightward, and the tip part 023 tilts rightward.

The vertical-bend knob lock lever 011 is attached to the case 014 so as to be vertically movable. The vertical-bend knob lock lever 011 stops rotation of the disk of the vertical-bend knob 012 to fix by sandwiching the disk of the vertical-bend knob 012, for example.

Each of the disks of the vertical-bend knob 012 and the horizontal-bend knob 013 is provided with a knob-position marker 015.

The case 014 of the ultrasound probe is provided with a center-position marker 016. When the knob-position marker 015 of the disk of the vertical-bend knob 012 coincides with the center-position marker 016 (as shown in Section A of FIG. 1), the bending part 022 is not bent backward or forward, and the tip part 023 is not tilted backward or forward. When the knob-position marker 015 of the disk of the horizontal-bend knob 013 coincides with the center-position marker 016 (as shown in Section A of FIG. 1), the bending part 022 is not bent rightward or leftward, and the tip part 023 is not tilted rightward or leftward. In this embodiment, the knob-position marker 015 and the center-position marker 016 are disposed in order to make it easy to grasp the state of the tip part 023. However, the ultrasound probe of this embodiment is capable of operating without these markers.

Further, the ultrasound probe according to this embodiment is connected to the ultrasound diagnosis apparatus by cable via the connector part. The electric signals converted from the ultrasound echo by the ultrasound transducer 024 are conveyed in the cable passing through the bending part 022, the guiding hollow tube part 021, the case 014 and the connector part, and outputted to the transceiver part of the ultrasound diagnosis apparatus.

(Configuration of Fixing Part of Horizontal-Bend Knob)

Figure 2:
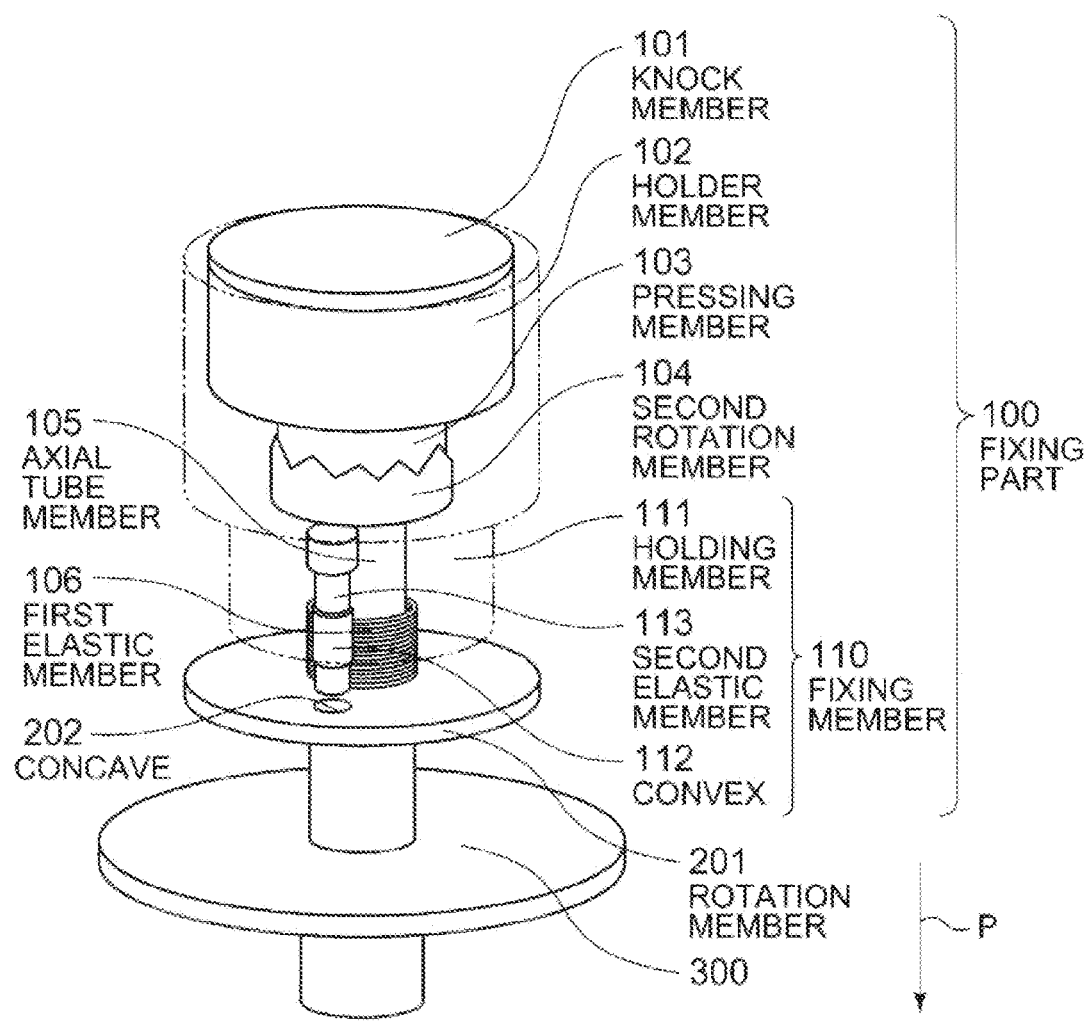
FIG. 2 is a perspective view schematically showing a fixing part according to a first embodiment taken from one direction.
Figure 3:
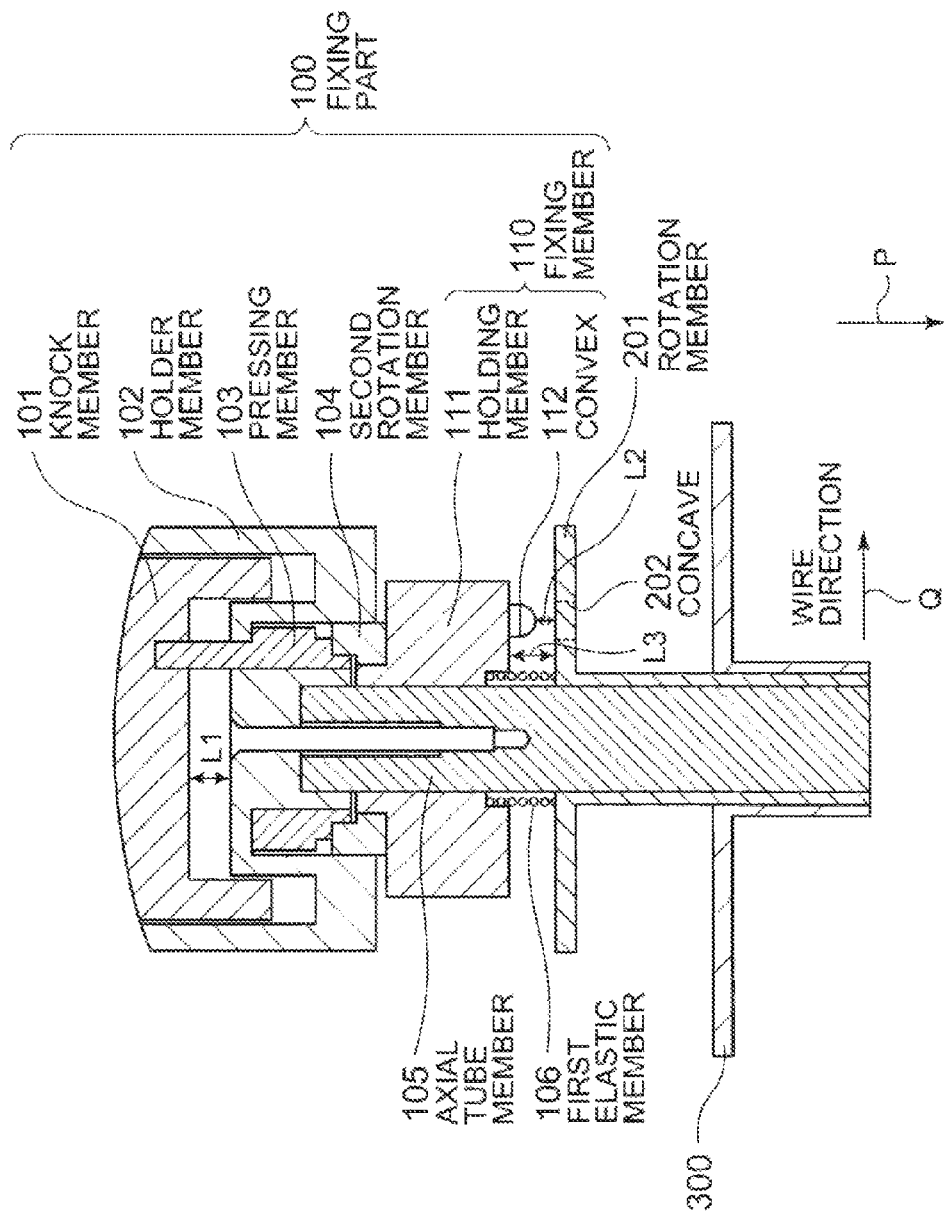
FIG. 3 is a cross sectional view schematically showing the fixing part according to the first embodiment.
Figure 4:
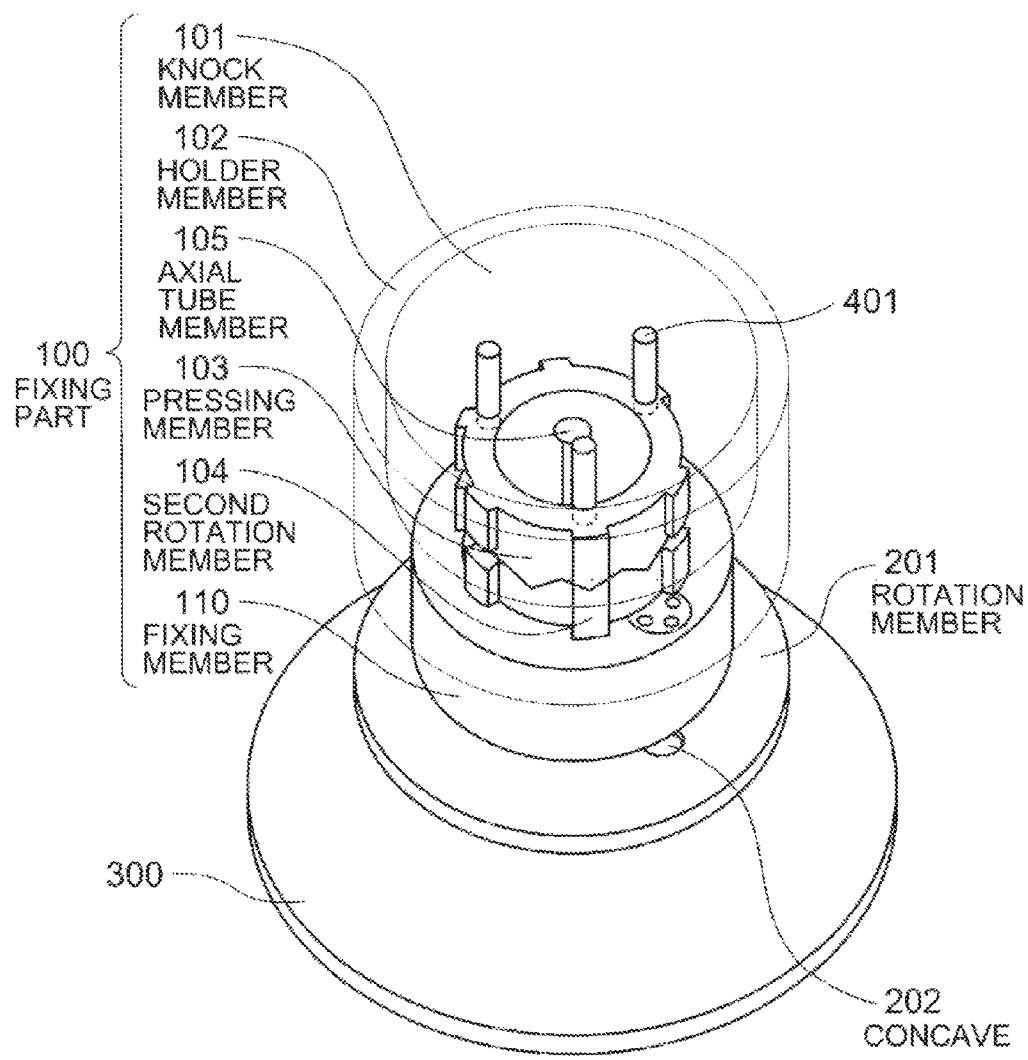
FIG. 4 is a perspective view schematically showing the fixing part according to the first embodiment taken from the other direction.

Next, a mechanism for locking the disk of the horizontal-bend knob 013 to inhibit rotation thereof will be described in detail with reference to FIGS. 2, 3 and 4. FIG. 2 is a perspective view schematically showing the fixing part according to this embodiment taken from one direction. FIG. 3 is a cross sectional view schematically showing the fixing part according to this embodiment. FIG. 4 is a perspective view schematically showing the fixing part according to this embodiment taken from the other direction.

FIGS. 2, 3 and 4 schematically show Section A of FIG. 1 in the magnified state. The disk of the horizontal-bend knob 013 in FIG. 1 corresponds to a rotation member 201 in FIGS. 2, 3 and 4. Moreover, the disk of the vertical-bend knob 012 to which the wires for tilting the tip part 023 are attached is a disk 300 in FIGS. 2, 3 and 4. For convenience of description, an arrow P direction shown in FIGS. 2 and 3 will be referred to as the "downward direction" hereinafter. A direction opposite to the arrow P direction will be referred to as the "upward direction."

An axial tube member 105 is a rod-like member. The axial tube member 105 is fixed to the case 104.

As shown in FIG. 4, the knock member 101 is coupled to the pressing member 103, which will be described later, by three support columns 401. As shown in FIG. 3, the support columns 401 are pierced through the holder member 102 and fixed to the pressing member 103.

The knock member 101 is capable of vertically moving along the axial tube member 105. When moving downward, the knock member 101 can move until coming in contact with the holder member 102. That is to say, the knock member 101 can move a distance L1 shown in FIG. 3.

Figure 5:
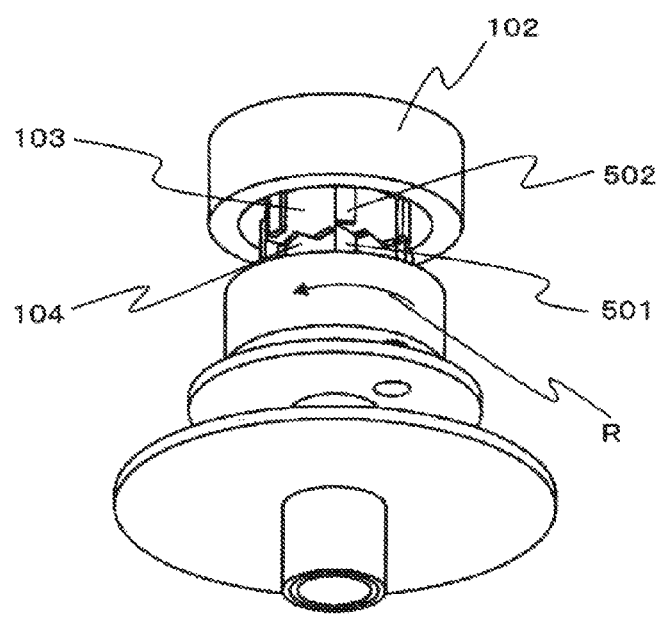
FIG. 5 is a perspective view showing the peripheries of a second rotation member and a pressing member exposed by displacing a holder member.

The lower plane, which is a plane in contact with the second rotation member 104, of the pressing member 103 has a shape that fits with a triangular wave pattern (refer to as "mountains and valleys" hereinafter) of the second rotation member 104, i.e., has similar mountains and valleys as the upper plane of the second rotation member 104. FIG. 5 is a perspective view showing the peripheries of the second rotation member 104 and the pressing member 103 exposed by displacing the holder member 102. Moreover, the pressing member 103 has a protrusion 502 on a plane (refer to as a "periphery" hereinafter) opposite to a place facing the axial tube member 105. The pressing member 103 directly receives a press by the knock member 101 via the support columns 401 and vertically moves along the axial tube member 105. Therefore, the pressing member 103 vertically moves the distance L1 along the axial tube member 105 in the same manner as the knock member 101.

Figure 7:
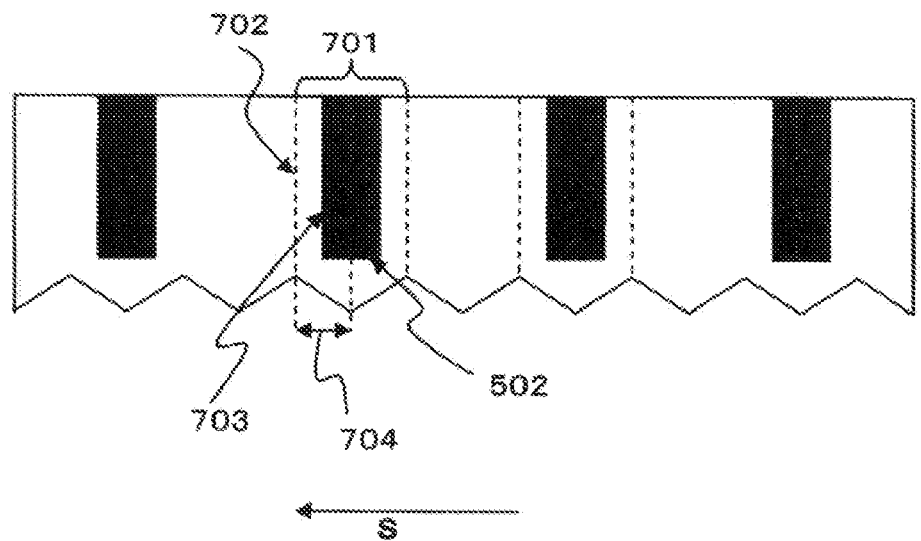
FIG. 7 is a developed view of the periphery of the pressing member.
Figures 10A, 10B:
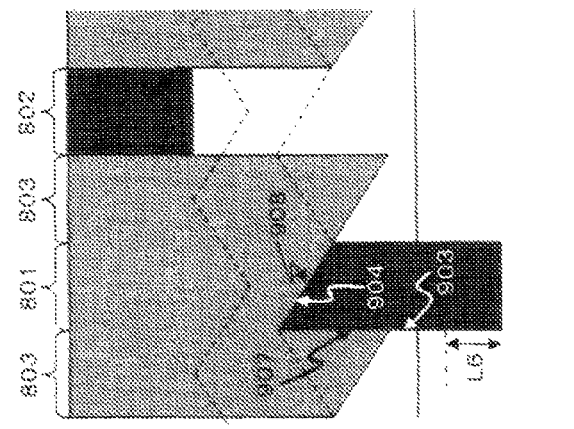
FIG. 10A is a view showing a fitting state of the holder member, the pressing member and the second rotation member, with a protrusion of the second rotation member housed in a groove of the holder member.
FIG. 10B is a view showing a fitting state of the holder member, the pressing member and the second rotation member, when the pressing member has fully moved toward the second rotation member in a first press.

FIG. 7 is a developed view of the periphery of the pressing member 103. Black portions are the protrusions 502. As shown in FIG. 7, the protrusion 502 is formed by protruding the central portion of a mountain portion 701, which is a portion forming a single mountain (simply referred to as a "mountain portion" hereinafter) in the mountains and valleys on the periphery of the pressing member 103. The protrusion 502 may be placed so that the side of the protrusion 502 in the rotation direction (arrow S direction) of the second rotation member 104 is located between the peak of the mountain portion 701 and a side 702 of the mountain portion 701, i.e., located in a distance 704. As shown in FIG. 10A, the protrusion 502 is housed in a groove 802 of the holder member 102 described later. The protrusion 502 may have any shape as far as it having a shape with enough width to be housed in the groove 802 of the holder member 102. The protrusion 502 is housed in the groove of the holder member 102, whereby the pressing member 103 is inhibited from rotationally moving around the axial tube member 105.

That is to say, the pressing member 103 is fixed with respect to a direction orthogonal to the axial tube member 105. Thus, it is preferred that the protrusion 502 has a width that is as close to the width of the groove as possible and that allows free vertical movement in the groove.

Although a plurality of protrusions 502 are disposed in order to securely inhibit the pressing member 103 from rotating in this embodiment, it is enough to dispose at least one protrusion 502. Since the pressing member 103 vertically moves the distance L1 as described above, the protrusion 502 also vertically moves the distance L1.

The rotation member 201 is equivalent to the disk attached to the axial center of the horizontal-bend knob 013. The axial tube member 105 is pierced through the center of the rotation axis of the rotation member 201. The rotation member 201 is placed so as to rotate around the axial tube member 105. Moreover, the rotation member 201 is fixed so as not to move in the vertical direction. Further, the rotation member 201 is provided with a concave 202, which is a vertical through hole.

Although the concave 202 is a through hole in this embodiment, the concave 202 may be a dent that is opened on the side facing a fixing member 110 but not pierced. Wires are connected to the downward end of the rotation member 201. The wires extend in a wire direction Q (refer to FIG. 3) to be connected to the rightward and leftward ends of the tip part 023 in FIG. 1. Rotation of the rotation member 201 pulls the wires, and rightward and leftward bend of the bending part 022 tilts the tip part 023 rightward and leftward. That is to say, when the rotation member 201 is fixed and inhibited from rotating, the tip part 023 cannot tilt rightward or leftward.

The fixing part 100, as shown in FIGS. 2, 3 and 4, includes a knock member 101, a holder member 102, a pressing member 103, a second rotation member 104, and a fixing member 110.

The fixing member 110 includes a holding member 111, a convex 112, and a second elastic member 113.

The convex 112 has a rod-like shape. The convex 112 has a diameter to fit into the concave 202. When the bending part 022 is not bent rightward or leftward and the tip part 023 is not tilted rightward or leftward, the convex 112 faces the concave 202.

The holding member 111 is in contact with the axial tube member 105. The holding member 111 is placed so as to be vertically movable along the axial tube member 105. Moreover, the holding member 111 fixed with respect to a direction orthogonal to the axial tube member 105 (the rotation direction of the rotation member 201). Specifically, a protrusion is disposed to a plane of the holding member 111 in contact with the axial tube member 105, and a vertical groove for housing the protrusion is disposed to the axial tube member 105, for example. Such a configuration allows the holding member 111 to vertically move along the axial tube member 105, but fixes the holding member 111 so as not to rotate around the axial tube member 105. As described later, when the operator presses the knock member 101 downward, the holding member 111 directly receives a force via the support columns 401, the pressing member 103 and the second rotation member 104, and moves downward, whereby the holding member 111 moves the distance L1 downward along the axial tube member 105 in the same manner as the knock member 101. A distance L3 when the holding member 111 is fully away from the rotation member 201 (when the protrusion 501 of the second rotation member 104 is housed in the groove 802 of the holder member 102 as shown in FIG. 10A described later: FIG. 10A is a view showing a fixing state of the holder member 102, the pressing member 103 and the second rotation member 104 with the protrusion 501 of the second rotation member 104 housed in the groove 802 of the holder member 102) is longer than the distance L1. Consequently, the holding member 111 does not come in contact with the rotation member 201 before the knock member 101 comes in contact with the holder member 102.

The holding member 111 has a hole to house the convex 112.

Between the hole of the holding member 111 and the convex 112, a second elastic member 113 for pressing the convex 112 in the protrusion direction is placed. The second elastic member 113 presses the convex 112 downward. Moreover, the hole of the holding member 111 is provided with a mechanism that prevents the convex 112 from slipping off the hole. This mechanism can be configured by, for example, disposing a protrusion to the periphery of the convex 112 closer to the second elastic member 113, forming the hole of the holding member 111 so as to have a size including the protrusion, and configuring the opening of the hole so as to allow the convex 112 to pass through and so as to catch the protrusion. The hole of the holding member 111 is positioned in a place that, when the convex 112 fits into the concave 202, the bending part 022 of FIG. 1 is not bent in the horizontal direction and the tip part 023 is not tilted in the horizontal direction. Therefore, the convex 112 fits into the concave 202 only when the bending part 022 is not bent in the horizontal direction and the tip part 023 is not tilted in the horizontal direction, whereby the rotation member 201 is locked so as not to rotate.

Figures 10C, 10D:
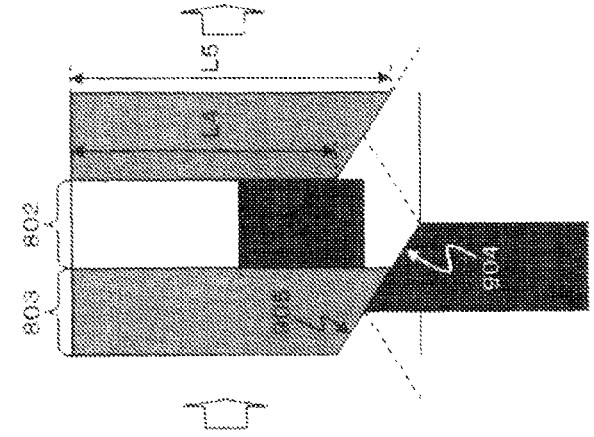
FIG. 10C is a view showing a fitting state of the holder member, the pressing member and the second rotation member, when the second rotation member has moved toward the pressing member and has come in contact with the protrusion of the holder member in the first press.
FIG. 10D is a view showing a fitting state of the holder member, the pressing member and the second rotation member, when the protrusion of the second rotation member has stopped in a shallow groove of the holder member in the first press.

A distance L2 between the convex 112 and the concave 202 when the holding member 111 is fully away from the rotation member 201 is shorter than a distance that the holding member 111 moves before coming close to the position fully away from the rotation member 201 and stopping (a distance L6 that the protrusion 501 of the second rotation member 104 moves before stopping in the groove 801 of the holder member 102 as shown in FIG. 10D described later: FIG. 10D is a view showing a fitting state of the holder member 102, the pressing member 103 and the second rotation member 104 when the protrusion 501 of the second rotation member 104 stops in the groove 801 of the holder member 102). Therefore, when the upward movement of the second rotation member 104 stops in the groove 801, the convex 112 fits into the concave 202, whereby the rotation member 201 is locked and inhibited from rotationally moving in the direction orthogonal to the axial tube member 105 of the rotation member 201. Therefore, it is preferred that the distance L2 allows the convex 112 to fit into the concave 202 when the holding member 111 comes close to the rotation member 201 and stops. Further, the distance L2 is enough to allow the convex 112 to rotate without coming in contact with the rotation member 201.

The first elastic member 106 is placed between the rotation member 201 and the fixing member 110. Since the rotation member 201 is fixed with respect to the vertical direction along the axial tube member 105, the first elastic member 106 presses the fixing member 110 upward. That is to say, the first elastic member 106 applies a force that separates the holding member 111 from the rotation member 201.

The second rotation member 104 is placed so as to be in contact with the upper part of the holding member 111. The second rotation member 104 is rotatable around the axial tube member 105. Moreover, the second rotation member 104 vertically moves along the axial tube member 105 in contact with the fixing member 110. As described later, when the operator presses the knock member 101 downward, the second rotation member 104 directly applies a force via the support columns 401 and the pressing member 103, and moves downward. Therefore, the second rotation member 104 vertically moves the distance L1 along the axial tube member 105 in the same manner as the knock member 101.

As shown in FIG. 5, the second rotation member 104 has the protrusion 501 on a plane opposite to the axial tube member 105 (refer to as a "periphery" hereinafter). Further, the upper part of the second rotation member 104, which is a plane in contact with the pressing member 103, has a shape of mountains and valleys as shown in FIG. 5.

FIG. 6A is a developed view of the periphery of the second rotation member 104 according to this embodiment. FIG. 6B is a plan view of the second rotation member 104 according to this embodiment taken from the side of the pressing member 103 (from above). Black portions shown in FIGS. 6A and 6B are the protrusions 501. As shown in FIG. 6A, the protrusion 501 is formed by protruding the right half of a mountain portion 601 in FIG. 6. The mountain portion 601 is a single mountain portion in the mountains and valleys on the periphery of the second rotation member 104 (simply referred to as a "mountain portion" hereinafter). A side of the protrusion 501 close to the pressing member 103 has the same tilt as the mountain of the second rotation member 104.

In this embodiment, the protrusion 501 is disposed to the right half of the mountain portion 601, whereby the second rotation member 104 rotates around the axial tube member 105 in an arrow S direction shown in FIGS. 5 and 6A. In a case where the protrusion 501 is disposed to the left half of the mountain portion 601, the second rotation member 104 rotates around the axial tube member 105 in a direction opposite to the arrow S direction. Although the protrusion 501 is formed by simply protruding part of the mountain portion 601 in this embodiment, the protrusion 501 may have any shape as far as the plane close to the pressing member 103 protrudes at the same tilt as the mountain portion 601. However, the width of the protrusion 501 in the arrow S direction needs to be a length equal to or less than the width of the right half of the mountain in this embodiment. Thus, the protrusion 501 can be housed in the groove of the holder member 102. As shown in FIG. 6A, the mountain portion 601 with the protrusion 501 and a mountain portion 602 without the protrusion 501 are alternately arranged around the second rotation member 104. As described before, since the pressing member 103 moves the distance L1 and the second rotation member 104 vertically moves the distance L1, the protrusion 501 on the second rotation member 104 also vertically moves the distance L1. Every time the second rotation member 104 moves the distance L1 downward and then returns upward, it rotates for one groove of the holder member 102, which will be described later.

Figure 8:
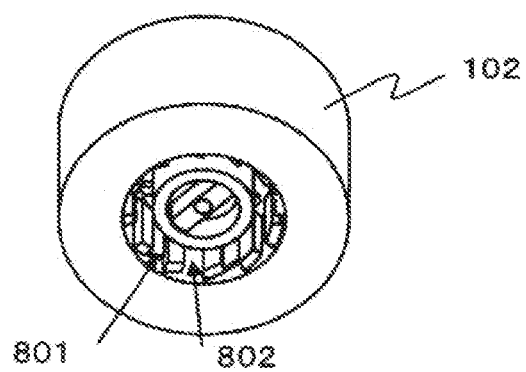
FIG. 8 is a perspective view of the holder member taken from below.

The holder member 102 has a shape that covers the pressing member 103 and the second rotation member 104 as shown in FIGS. 2 and 3. A plane of the holder member 102 close to the axial tube member 105 in contact with the pressing member 103 and the second rotation member 104 has grooves as shown in FIG. 8. FIG. 8 is a perspective view showing the holder member 102 taken from below. The holder member 102 has a shallow groove 801 and a deep groove 802 as shown in FIG. 8.

Further, the holder member 102 is fixed to the axial tube member 105. That is to say, the holder member 102 does not vertically move along the axial tube member 105 or rotate in the direction orthogonal to the axial tube member 105. Further, the holder member 102 has three holes on the upper plane thereof so as to pass the support columns 401.

Figure 9:
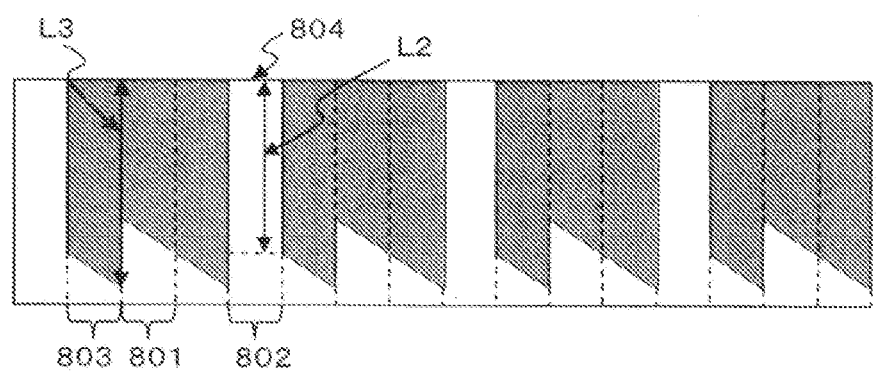
FIG. 9 is a developed view of a plane of the holder member in contact with the pressing member and the second rotation member.

FIG. 9 is a developed view showing a plane of the holder member 102 in contact with the pressing member 103 and the second rotation member 104 (refer to an "inner plane" hereinafter). In FIG. 9, a protruding portion of the inner plane of the holder member 102 is shown in gray, and a portion that does not protrude is shown in white. As shown in FIG. 9, on the inner plane of the holder member 102, the grooves 801 and the grooves 802 are alternately sandwiched one by one by protrusions 803 in the rotation direction orthogonal to the axial tube member 105. Moreover, the groove 801 and the groove 802 are formed by grooving along the axial tube member 105. Further, the groove 801 and the groove 802 are open downward.

The groove 802 houses the protrusion 502 of the pressing member 103. Here, as shown in FIG. 7, a side 703 of the protrusion 502 is off a side 702 of a mountain portion 701. Therefore, as shown in FIG. 10A, the tilt portions of the holder member 102 and the mountains and valleys of the pressing member 103 are placed off each other. Moreover, an upper side 804 of the groove 802 shown in FIG. 9 is closed. Therefore, in a case where the pressing member 103 receives a press from below and moves upward, the protrusion 502 of the pressing member 103 stops moving at the upper side 804 of the groove 802. When the upward movement of the pressing member 103 is thus stopped by the holder member 102, the upward movement of the knock member 101, the second rotation member 104 and the fixing member 110 is also stopped in a state where the protrusion 502 is in contact with the upper side 804 of the groove 802. Moreover, protrusions 803 are placed on both sides of the groove 802, respectively. The protrusion 803 inhibits the protrusion 502 from moving in the direction orthogonal to the axial tube member 105. Further, a length L4 in the groove 802 is longer than the distance L1 that the protrusion 502 moves. Therefore, as shown in FIG. 10B, even if the protrusion 502 in contact with the upper side 804 moves the distance L1 downward, it does not come off the groove 802. Here, FIG. 10B is a view showing a fitting state of the holder member 102, the pressing member 103 and the second rotation member 104 when the pressing member 103 moves toward the rotation member 104 (downward) at the maximum.

As shown in FIG. 9, the lower side of the protrusion 803 is tilted upward in the rotation direction of the second rotation member 104 (the arrow S direction in FIG. 7). The angle of the tilt is equal to the angle of tilt of the protrusion 501 on the second rotation member 104. A length L5 of a side of the protrusion 803 close to the groove 802 is longer than the distance L1. Therefore, as shown in FIG. 10B, even if the protrusion 502 in contact with the upper side 804 moves the distance L1 downward, it does not come off the groove 802. Further, the length L5 is shorter than a length obtained by adding the distance L1 and a distance to the upper side 804 from the protrusion 501 of the second rotation member 104 when the protrusion 502 is in contact with the upper side 804.

Therefore, as shown in FIG. 10B, when the protrusion 502 moves the distance L1 from the state where the protrusion 502 stops in contact with the upper side 804, the protrusion 501 comes outside the groove 802.

The groove 801 is shallower on the upper side 804 as shown by gray portion in FIG. 9. This portion will be referred to as a "shallow portion of the groove 801" hereinafter. The lower side of the shallow portion of the groove 801 has the same angle as the protrusion 803, and the protrusion 803 and the shallow portion of the groove 801 form a continuous tilt. When the upper side of the protrusion 501 of the second rotation member 104 comes in contact with the lower side of the shallow portion of the groove 801, the upward movement of the protrusion 501 is stopped. When the shallow portion of the groove 801 comes in contact with the protrusion 501 of the second rotation member 104, as shown in FIG. 10D, the shallow portion of the groove 801 stops the protrusion 501 at a position a distance L6 below the position of the protrusion 501 in FIG. 10A. As shown in FIG. 8, the groove 801 has a more depth than the protrusion 803 in this embodiment, and this depth needs to be thick enough to come in contact with the protrusion 501. The shallow portion of the groove 801 and the projection of the protrusion 803 may have the same depth.

Next, the operation of the fixing part 100 will be described as a whole. A direction that the second rotation member 104 rotates in the direction orthogonal to the axial tube member 105, i.e., an arrow R direction in FIG. 5 will be referred to as a "rotation direction" hereinafter. The operation from a state where the protrusion 501 of the second rotation member 104 is housed in the groove 802 of the holder member 102 will be described below. That is to say, the following description starts from the state of FIG. 10A. The starting state is the initial state. Moreover, the position of each member in the initial state will be referred to as the initial position.

(First Press by Operator)

The operator presses the knock member 101 downward.

The knock member 101 presses the pressing member 103 downward via the support columns 401. After moving the distance L1 from the initial position, the knock member 101 comes in contact with the holder member 102 and stops.

The pressing member 103 receives a downward force from the knock member 101 and moves downward. As shown in FIG. 10A, the pressing member 103 is in contact with the second rotation member 104 at a side 901. The second rotation member 104 receives an upward press from the first elastic member 106 via the fixing member 110. Therefore, to the second rotation member 104, a force to move in a direction with less friction, i.e., along the tilt of the pressing member 103 is applied so that the mountains and valleys of the pressing member 103 and the mountains and valleys of the second rotation member 104 perfectly fit each other. Consequently, the second rotation member 104 receives a force in the rotation direction. On the other hand, the protrusion 501 of the second rotation member 104 is housed in the groove 802 of the holder member 102. Therefore, when the second rotation member 104 rotates in the rotation direction as the second rotation member moves along the tilt of the pressing member 103, the protrusion 501 comes in contact with a side 902 of the protrusion 803 and stops rotation. Then, the second rotation member 104 does not rotate, and a force to move downward of the pressing member 103 is transmitted to the second rotation member 104. The pressing member 103 moves the distance L1 downward.

The second rotation member 104 receives a downward force from the pressing member 103 and moves downward. The second rotation member 104 moves the distance L1 downward. The protrusion 501 of the second rotation member 104 also moves the distance L1 downward. A length obtained by adding the distance L1 to the initial position of a side 903 of the protrusion 501 at the initial position is longer than the length L5 of the side 902 of the protrusion 803. Therefore, the upper end of the side 903 in the rotation direction of the protrusion 501 exceeds the lower end of the side 902 of the protrusion 803. Consequently, the protrusion 803 is no more in contact with the protrusion 501 in the rotation direction. Then, the second rotation member 104 moves in the direction with less friction. That is to say, the mountains and valleys of the second rotation member 104 move along the tilts of the pressing member 103. Consequently, the second rotation member 104 rotates in the rotation direction. As the mountains and valleys of the second rotation member 104 perfectly fit the mountains and valleys of the pressing member 103 as shown in FIG. 10B, the second rotation member 104 receives a frictional force and stops rotating in the rotation direction.

The holding member 111 receives a downward force from the second rotation member 104 and moves downward. Since the second rotation member 104 moves the distance L1, the holding member 111 also moves the distance L1.

The convex 112 receives a downward force from the holding member 111 and moves downward. Since the holding member 111 moves the distance L1, the convex 112 also moves the distance L1. The distance L2 between the convex 112 and the rotation member 201 is shorter than the distance L1. Therefore, in a case that the concave 202 is facing the convex 112, the convex 112 fits into the concave 202. On the contrary, in a case that the concave 202 is not facing the convex 112, the convex 112 comes in contact with a spot other than the concave 202 on a plane of the rotation member 201 with the concave 202 opened. In this case, the convex 112 receives an upward force from the rotation member 201. Then, the second elastic member 113 receives an upward force from the convex 112, whereby the second elastic member 113 is compressed. The second elastic member 113 presses the convex 112 downward. The convex 112 presses the rotation member 201 downward.

In this case, since the convex 112 does not fit into the concave 202, the rotation member 201 is not locked and is not inhibited from rotating.

(Release of First Press by Operator)

The operator releases the knock member 101 to release the pressing force.

The first elastic member 106 presses the holding member 111 upward.

The second rotation member 104 receives the upward force from the first elastic member 106 via the holding member 111. The second rotation member 104 moves upward. An upper slope side 904 of the protrusion 501 of the second rotation member 104 comes in contact with a lower slope side 905 of the protrusion 803 of the holder member 102 as shown in FIG. 10C. FIG. 10C is a view showing a fitting state of the holder member 102, the pressing member 103 and the second rotation member 104, when the second rotation member 104 has moved toward the pressing member 103 (upward) and has comes in contact with the protrusion 803 of the holder member 102. The protrusion 501 moves in the direction with less friction, namely, along the slope of the side 905.

Consequently, the second rotation member 104 rotates in the rotation direction.

The protrusion 501 of the second rotation member 104 moves along the slope of the side 905 of the protrusion 803, and moves into the groove 801. As shown in FIG. 10D, the side 903 in the rotation direction of the protrusion 501 comes in contact with a side 907 of the protrusion 803 of the holder member 102, and stops the movement in the rotation direction by the friction. Moreover, the upper side 904 of the protrusion 501 comes in contact with a lower side 908 of the shallow portion of the groove 801, and stops the upward movement by the friction.

Consequently, the second rotation member 104 stops moving in both the rotation direction and the upward direction. Since the protrusion 501 moves the distance L1 downward by the press of the operator and then moves upward until coming in contact with the shallow portion of the groove 801, the protrusion 501 finally moves a distance L6 downward from the initial state and stops as shown in FIG. 10D. Consequently, the second rotation member 104 also stops in a state that it has been moved the distance L6 downward from the initial state.

The pressing member 103 receives a force from the second rotation member 104 and moves upward. When the protrusion 501 of the second rotation member 104 hits the shallow portion of the groove 801 of the holder member 102 and stops, the pressing member 103 stops because it receives no upward force from the second rotation member 104.

The knock member 101 receives the force from the pressing member 103 via the support columns 401 and moves upward. When the protrusion 501 of the second rotation member 104 hits the shallow portion of the groove 801 of the holder member 102 and stops, the knock member 101 stops because it receives no upward force from the pressing member 103.

The holding member 111 receives a force from the first elastic member 106 and moves upward. When the protrusion 501 of the second rotation member 104 hits the shallow portion of the groove 801 of the holder member 102 and stops, the holding member 111 also stops because it is in contact with the second rotation member 104. As described before, the second rotation member 104 stops at a position moved the distance L6 downward from the initial position. Therefore, the holding member 111 also stops at a position moved the distance L6 downward from the initial position.

In a case where the convex 112 is fit in the concave 202, the convex 112 is pulled upward by the holding member 111, and stops at a position moved the distance L6 downward from the initial position. As described before, since the distance L6 is longer than the distance L2, the convex 112 stops at a position fit in the concave 202. Therefore, the fixing member 110 locks the rotation member 201. The rotation member 201 is inhibited from rotating. As described before, the convex 112 and the concave 202 are placed so as to fit each other in a state that the wires are not pulled either rightward or leftward by the rotation member 201. Therefore, in this case, it is possible to inhibit the operator from horizontally bending the bending part 022 and tilting the tip part 023.

In a case where the convex 112 is not fit in the concave 202, the second elastic member 113 compressed between the holding member 111 and the convex 112 is stretched. Therefore, the convex 112 does not move vertically. Moreover, since the distance L2 is longer than the distance L6, the second elastic member 113 presses the convex 112 downward. The convex 112 receives a downward force from the second elastic member 113, and keeps pressing downward the plane of the rotation member 201 with the concave 202 opened. In this state, the convex 112 is not fit in the concave 202, and the rotation member 201 is not locked. Thus, in a case that the operator rotates the rotation member 201 and the convex 112 reaches the position facing the concave 202, the convex 112 receives a downward force from the second elastic member 113 and fits into the concave 202. Consequently, the fixing part 100 locks the rotation member 201 and inhibits the rotation member 201 from rotating. As described before, the convex 112 and the concave 202 are placed so as to fit each other in a state that the wires are not pulled either rightward or leftward by the rotation member 201. Therefore, the fixing part 100 locks the rotation member 201 at a position where the bending part 022 is not bent as well as the tip part 023 is not tilted in the horizontal direction. Consequently, it is possible to inhibit the operator from horizontally bending the bending part 022 and tilting the tip part 023 in the horizontal direction.

(Second Press by Operator)

The operator presses the knock member 101 downward.

The knock member 101 presses the pressing member 103 downward via the support columns 401. After moving the distance L1 from the initial position, the knock member 101 comes in contact with the holder member 102 and stops.

Figure 11C:
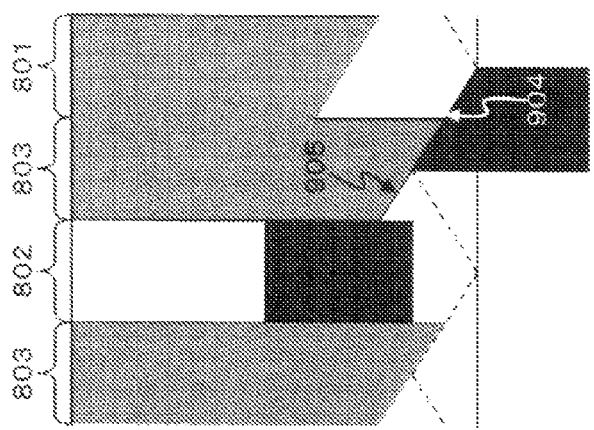
FIG. 11C is a view showing a fitting state of the holder member, the pressing member and the second rotation member, when the second rotation member has moved toward the pressing member and has come in contact with the protrusion of the holder member in the second press.

The pressing member 103 receives a downward force from the knock member 101 and moves downward. As shown in FIG. 11A, the side 901 of the pressing member 103 comes in contact with the upper side 904 of the protrusion 501 at a position of the distance L6 below the initial position. FIG. 11A is a view showing a fitting state of the holder member 102, the pressing member 103 and the second rotation member 104, when the pressing member 103 has moved toward the second rotation member 104 (downward) and has comes in contact with the mountains and valleys of the second rotation member 104 in a second press. Then, the second rotation member 104 receives an upward press from the first elastic member 106 via the fixing member 110. Therefore, to the second rotation member 104, a force to move in a direction with less friction, i.e., along the tilt of the pressing member 103 is applied so that the mountains and valleys of the pressing member 103 and the mountains and valleys of the second rotation member 104 perfectly fit each other. Consequently, the second rotation member 104 receives a force in the rotation direction. On the other hand, the protrusion 501 of the second rotation member 104 is housed in the groove 801 of the holder member 102. Therefore, when the second rotation member 104 moves along the tilt of the pressing member 103 and thereby rotates in the rotation direction, the protrusion 501 comes in contact with the side 907 of the protrusion 803 and stops rotation. Thus, the second rotation member 104 does not rotate, and a force to move downward of the pressing member 103 is transmitted to the second rotation member 104.

The pressing member 103 moves the distance L1 downward from the initial position.

The second rotation member 104 receives a downward force from the pressing member 103 and moves downward. The second rotation member 104 moves the distance L1 downward from the initial position.

The protrusion 501 of the second rotation member 104 also moves the distance L1 downward from the initial position. A length obtained by adding the distance L1 to the initial position of the upper end of the side 903 of the protrusion 501 is longer than the length L5 of the side 902 of the protrusion 803. Therefore, the upper end of the side 903 in the rotation direction of the protrusion 501 exceeds the lower end of the side 907 of the protrusion 803. Consequently, the protrusion 803 is no more in contact with the protrusion 501 in the rotation direction.

Thus, the second rotation member 104 moves in the direction with less friction. That is to say, the mountains and valleys of the second rotation member 104 move along the tilts of the pressing member 103. Consequently, the second rotation member 104 rotates in the rotation direction. As the mountains and valleys of the second rotation member 104 perfectly fit the mountains and valleys of the pressing member 103 as shown in FIG. 11B, the second rotation member 104 receives a frictional force and stops rotating in the rotation direction.

Figure 11B:
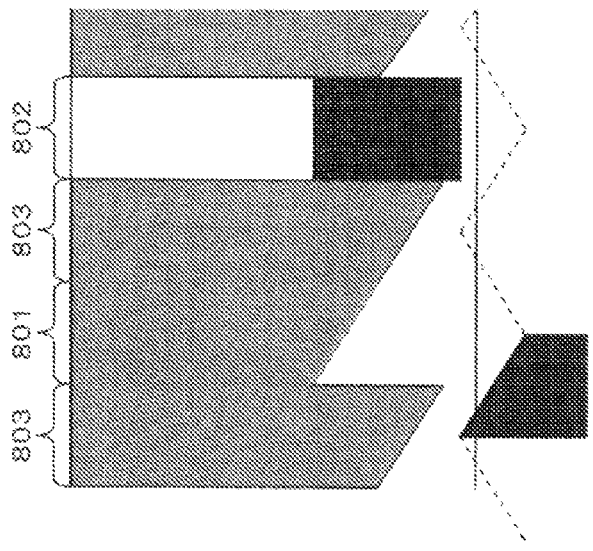
FIG. 11B is a view showing a fitting state of the holder member, the pressing member and the second rotation member, when the pressing member has fully moved toward the second rotation member in the second press.
Figure 11A:
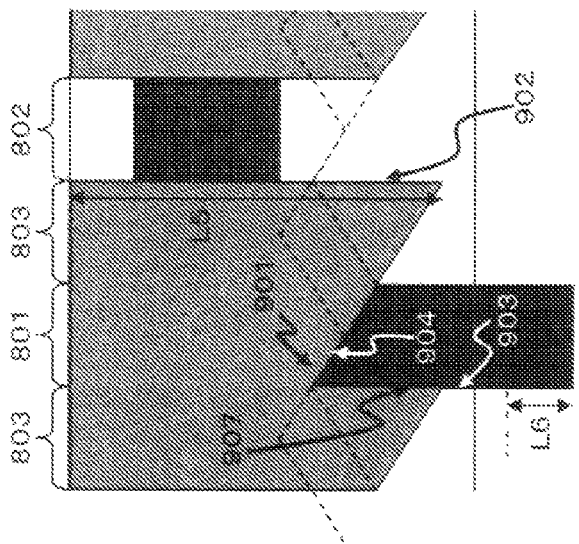
FIG. 11A is a view showing a fitting state of the holder member, the pressing member and the second rotation member, when the pressing member has moved toward the second rotation member and has come in contact with mountains of the second rotation member in a second press.

FIG. 11B is a view showing a fitting state of the holder member 102, the pressing member 103 and the second rotation member 104, when the pressing member 103 has fully moved toward the second rotation member 104 (downward) in the second press.

The holding member 111 receives a downward force from the second rotation member 104 and moves downward. Since the second rotation member 104 moves the distance L1, the holding member 111 also moves the distance L1 from the initial position.

The convex 112 receives a downward force from the holding member 111 and moves downward. Since the holding member 111 moves the distance L1 from the initial position, the convex 112 also moves the distance L1 from the initial position. Here, in a case that the concave 202 is fit with the convex 112, the convex 112 remains fit in the concave 202. Moreover, in a case where the convex 112 is in contact with a plane with the concave 202 opened of the rotation member at a spot other than the concave 202, the convex 112 keeps pressing downward while being in contact with the aforementioned plane.

(Release of Second Press by Operator)

The operator releases the knock member 101 to release the pressing force.

The first elastic member 106 presses the holding member 111 upward.

The second rotation member 104 receives the upward force from the first elastic member 106 via the holding member 111. The second rotation member 104 moves upward. The upper slope side 904 of the protrusion 501 of the second rotation member 104 comes in contact with the lower slope side 905 of the protrusion 803 of the holder member 102 as shown in FIG. 11C. FIG. 11C is a view showing a fitting state of the holder member 102, the pressing member 103 and the second rotation member 104, when the second rotation member 104 has moved toward the pressing member 103 (upward) and has comes in contact with the protrusion 803 of the holder member 102 in the second press. The protrusion 501 moves in a direction with less friction, namely, along the slope of the side 905. Consequently, the second rotation member 104 rotates in the rotation direction.

The protrusion 501 of the second rotation member 104 moves along the slope of the side 905 of the protrusion 803, and moves into the groove 802. As shown in FIG. 10A, the side 903 in the rotation direction of the protrusion 501 comes in contact with the side 902 of the protrusion 803 of the holder member 102, and stops the movement in the rotation direction by the friction. Moreover, the mountains and valleys of the second rotation member 104 come in contact with the mountains and valleys of the pressing member 103 at the side 901, and the upward movement is stopped by the friction. Consequently, the second rotation member 104 stops moving in both the rotation direction and the upward direction. The second rotation member 104 and the protrusion 501 return to the initial position.

The pressing member 103 receives a force from the second rotation member 104 and moves upward. When the upper side of the protrusion 502 of the pressing member 103 comes in contact with the upper side 804 of the groove 802 of the holder member 102, the upward movement of the protrusion 502 is stopped. Consequently, the movement of the pressing member 103 is also stopped. The protrusion 502 and the pressing member 103 return to the initial position.

The knock member 101 receives the force from the pressing member 103 via the support columns 401, and moves upward. When the protrusion 502 of the pressing member 103 comes in contact with the upper side 804 of the groove 802 of the holder member 102 and stops moving upward, the knock member 101 stops because it receives no upward force from the pressing member 103.

The holding member 111 receives the force from the first elastic member 106 and moves upward. When the protrusion 502 of the pressing member 103 comes in contact with the upper side 804 of the groove 802 of the holder member 102 and stops moving upward, the second rotation member 104 is stopped. Since the holding member 111 is contact with the second rotation member 104, the holding member 111 also stops. As described before, the second rotation member 104 returns to the initial position. Therefore, the holding member 111 also stops at the initial position.

In a case where the convex 112 is fit in the concave 202, the convex 112 is pulled upward by the holding member 111, and stops at the initial position. As described before, since the distance L3 is longer than the distance L2, the convex 112 stops away from the concave 202.

Therefore, the fixing member 110 releases lock of the rotation member 201, whereby the rotation member 201 can rotate.

In a case that the convex 112 is not fit in the concave 202, the second elastic member 113 compressed between the holding member 111 and the convex 112 is stretched. Therefore, the convex 112 remains in contact with the plane of the rotation member 201 with the concave 202 opened until the mechanism for preventing slip off the hole of the holding member 111 acts. When the mechanism for preventing the convex 112 from slipping off the hole of the holding member 111 acts, the convex 112 receives an upward force from the holding member 111, and moves upward. The convex 112 separates from the plane of the rotation member 201 with the concave 202 opened. Also in this case, the fixing member 110 is not locking the rotation member 201. Therefore, the rotation member 201 can rotate.

In this embodiment, in order to stop the holding member 111 in the vicinity of the rotation member 201 and make the convex 112 press the rotation member 201 even if the convex 112 is at a position where it does not fit into the concave 202, the second elastic member 113 is placed above the convex 112 so that only a part of the convex 112 can vertically move. This is because if the operator rotates the rotation member 201 in a state that the convex 112 is pressing the rotation member 201, the convex 112 automatically fits into the concave 202 when the concave 202 reaches a position facing the convex 112.

Therefore, if the above mechanism is not required, the ultrasound probe of the present invention can also operate with a configuration that the second elastic member 113 is eliminated and the convex 112 is integrated with the holding member 111.

Further, in this embodiment, the fixing part 100 is configured so that the rotation member 201 can be repeatedly locked and released by repetition of press by the operator from one direction. However, the fixing part 100 may have any configuration as far as the convex 112 of the fixing member 110 fixed with respect to in the rotation direction of the rotation member 201 fits into the concave 202 of the rotation member 201 in a state that the bending part 022 and the tip part 023 are not bent either rightward or leftward. For example, it is possible to configure to fit a rod-like convex piercing the fixing member 110 into a concave of the rotation member 201 by manually pressing the convex from behind.

Furthermore, in this embodiment, the fixing member 110 is provided with the convex 112, and the rotation member 201 is provided with the concave. However, the fixing member 110 may be provided with a concave, and the rotation member 201 may be provided with a convex. In this case, an elastic member is disposed behind the convex disposed to the rotation member 201, and the operator rotates the rotation member 201 in a state that the convex is pressing the fixing member 110 as in this embodiment, whereby the convex can automatically fit into the concave when the convex and the concave face each other.

Thus, the ultrasound probe according to this embodiment can lock the bend in the rightward and leftward directions only when the tip part is not bent rightward or leftward. Consequently, even if the tip part is inserted in the body cavity and the tilt of the tip part cannot be seen, the operator will not lock the horizontal bending part in a state that the tip part tilts rightward or leftward. Thus, the operator will not insert or remove the tip part inserted in the body cavity while the tip part tilts rightward and leftward, and it is possible to reduce the risk of damaging an insertion path by the tip part. Further, since the tip part can be locked without tilting rightward or leftward, it is possible to easily insert the ultrasound probe into the subject.

Second Embodiment

Next, an ultrasound probe according to a second embodiment will be described. The entire configuration of the ultrasound probe according to this embodiment is similar to that of the first embodiment. Moreover, the operation of fitting the convex of the fixing part into the concave of the rotation member is similar to that of the first embodiment.

Figure 12:
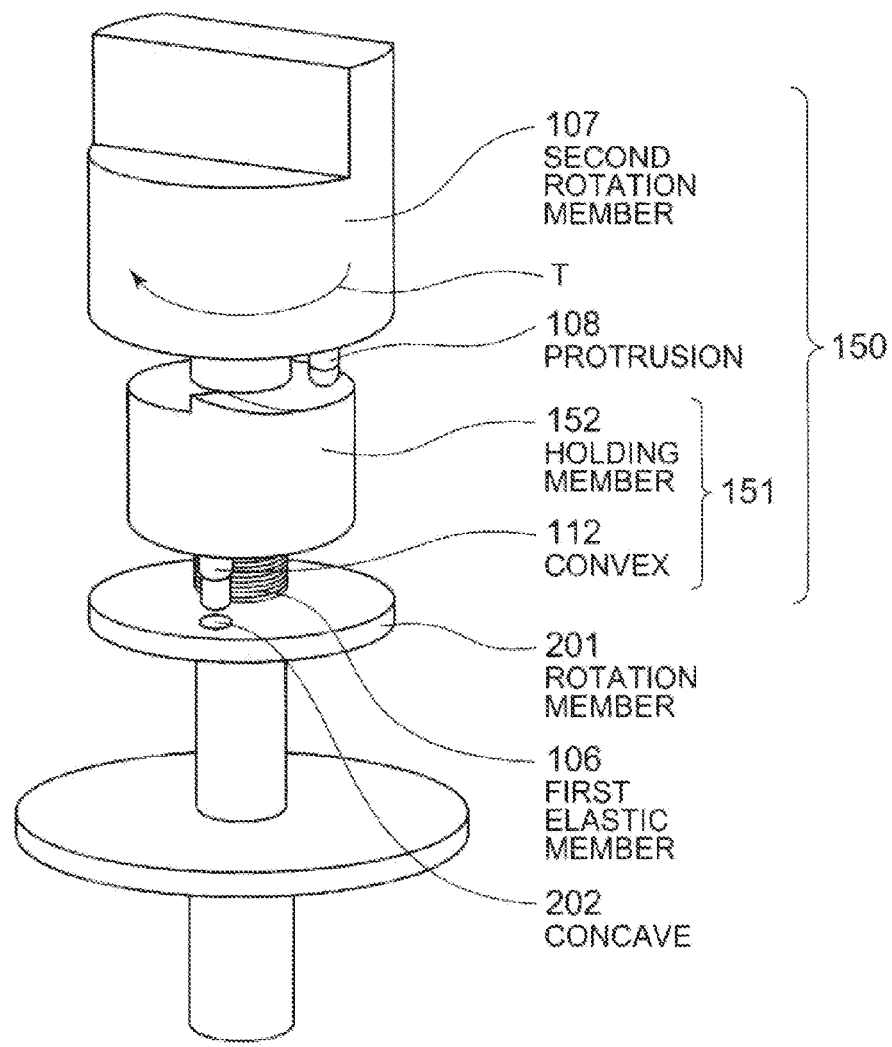
FIG. 12 is a perspective view of a fixing part and a bending part according to a second embodiment.
Figure 13:
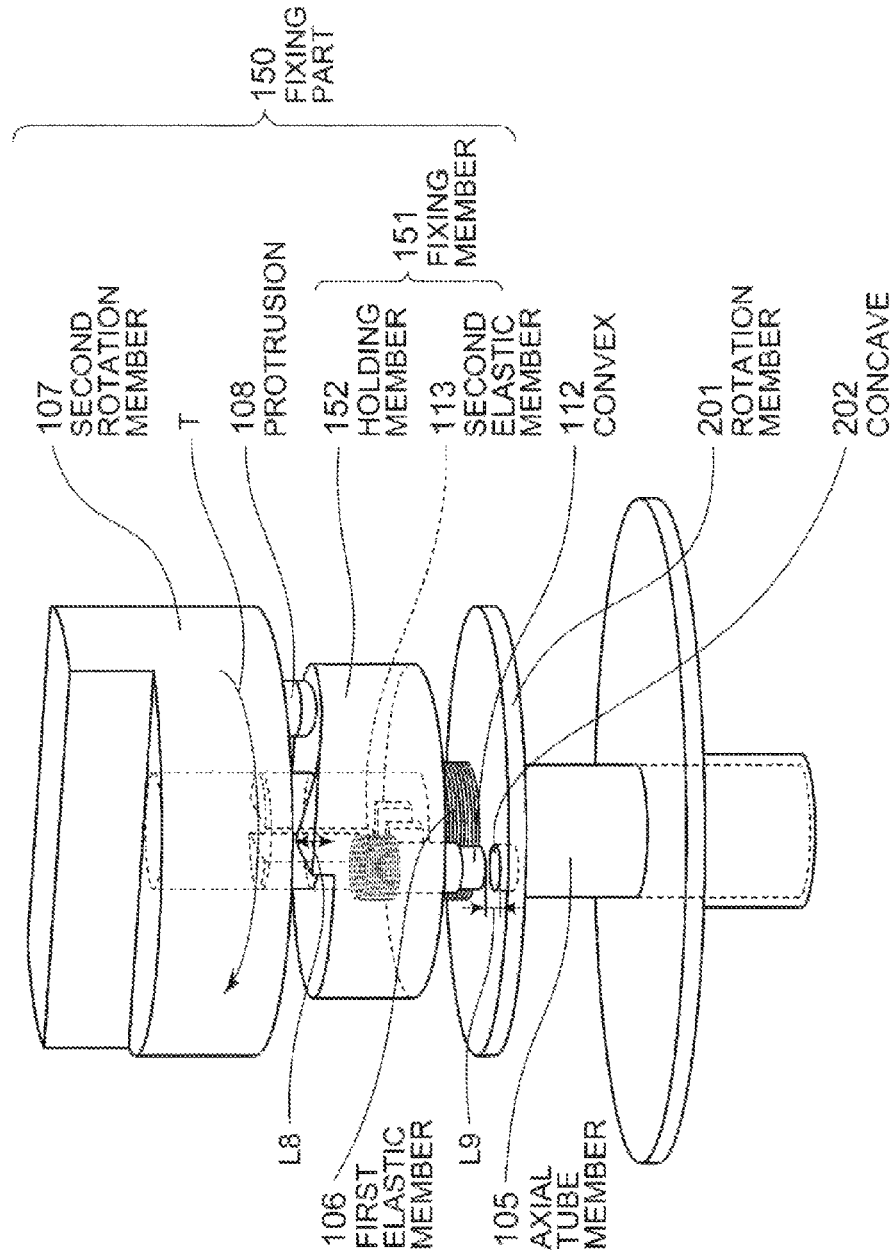
FIG. 13 is a perspective view of the fixing part and the bending part according to the second embodiment.

Hereinafter, with reference to FIGS. 12 and 13, a method for pressing a fixing member of a fixing part of the second embodiment in a rotation member direction will be majorly described below. FIG. 12 is a perspective view showing a fixing part and a bending part according to this embodiment. FIG. 13 is a perspective view showing the fixing part and the bending part according to this embodiment. In FIGS. 12 and 13, members having the same reference numerals as those of the first embodiment will have the same functions.

In the following description, a direction along the axial tube member 105 and seen from the rotation member 201 to a fixing part 150 will be referred to as an "upward direction." A direction along the axial tube member 105 and seen from the fixing part 150 to the rotation member 201 will be referred to as a "downward direction." A direction rotating from right to left through the front in FIGS. 12 and 13, namely, an arrow T direction will be referred to as a "rotation direction."

(Configuration of Fixing Part of Horizontal-Bend Knob)

The fixing part 150 includes a second rotation member 107, a protrusion 108, and a fixing member 151.

The second rotation member 107 is fixed with reference to a direction along the axial tube member 105. Moreover, the second rotation member 107 is placed so as to be capable of rotating an angle θ around the axial tube member 105 in a direction orthogonal to the axial tube member 105. A position that the second rotation member 107 is moved to the limit in a direction opposite to the rotation direction will be referred to as a "reference position" hereinafter. That is to say, the second rotation member 107 is capable of rotating the angle θ from the reference position in the rotation direction.

The second rotation member 107 has the protrusion 108 on a plane (lower plane) facing a holding member 152.

The fixing member 151 includes the holding member 152, a convex 112, and a second elastic member 113.

The relation of the holding member 152, the convex 112 and the second elastic member 113 is similar to that in the first embodiment.

The holding member 152 has a slope on a plane facing the second rotation member 107, which comes close to the second rotation member 107 in the rotation direction. The slope is placed so that the protrusion 108 is positioned near the opposite side to the top of the slope with respect to the rotation direction when the second rotation member 107 moves the angle θ in the rotation direction from the reference position.

Consequently, the protrusion 108 will not fall off the slope in the rotation direction even if the second rotation member 107 rotates.

Furthermore, a vertical distance L8 (refer to FIG. 13) from a vertical position of the protrusion 108 at the reference position to a position of the protrusion 108 after the angle θ rotation from the reference position is longer than a distance between the convex 112 and the concave 202 when the protrusion 108 is at the reference position.

Therefore, in a case that the second rotation member 107 rotates the angle θ from the reference position, the holding member 152 moves the distance L8 downward. In a case that the convex 112 and the concave 202 are facing each other, the convex 112 fits into the concave 202 when the second rotation member 107 rotates the angle θ from the reference position. In a case that the convex 112 and the concave 202 are not facing each other, the convex 112 comes in contact with the rotation member 201 and presses the rotation member 201.

Further, a distance L9 is a distance enough for the rotation member 201 to rotate without the convex 112 in contact with the rotation member 201. Therefore, the rotation member 201 can rotate when the second rotation member 107 is at the reference position.

Next, the operation of the fixing part 150 will be described as a whole. The following description is a description of the operation from a state that the second rotation member 107 is at the reference position.

A position of each member at the initial position will be referred to as the initial position.

(Rotation in Rotation Direction from Reference Position)

The operator rotates the second rotation member 107 the angle θ in the rotation direction.

The second rotation member 107 rotates the angle θ in the rotation direction.

The protrusion 108 disposed to the second rotation member 107 also moves from the reference position in the rotation direction. The protrusion 108 moves on the slope of the holding member 152 in the rotation direction, namely, in a direction ascending the slope. As the protrusion 108 moves on the slope in the rotation direction, the protrusion 108 gradually moves the holding member 152 downward. The second rotation member 107 stops after moving the angle θ from the reference position. The protrusion 108 stops near the top of the slope on the opposite side with respect to the rotation direction.

The holding member 152 gradually descends for a height of the slope as the protrusion 108 moves on the slope in the rotation direction.

After the second rotation member 107 moves the angle θ from the reference position, the holding member 152 stops at a position moved the distance L8 downward from the initial position.

The convex 112 fits into the concave 202 as in the first embodiment, or presses the plane (upper plane) of the rotation member 201 with the concave 202 opened.

(Rotation to Reference Position in Direction Opposite to Rotation Direction)

The operator rotates the second rotation member 107 the angle θ in a direction opposite to the rotation direction.

The second rotation member 107 rotates the angle θ in the direction opposite to the rotation direction.

The protrusion 108 disposed to the second rotation member 107 also moves in the direction opposite to the rotation direction from the position near the top of the slope on the opposite side with respect to the rotation direction. The protrusion 108 moves on the slope of the holding member 152 in the direction opposite to the rotation direction, namely, in a direction descending the slope. As the protrusion 108 moves on the slope in the direction opposite to the rotation direction, the protrusion 108 gradually moves the holding member 152 upward. The second rotation member 107 and the protrusion 108 stop at the reference position.

The holding member 152 gradually ascends for a height of the slope as the protrusion 108 moves on the slope in the direction opposite to the rotation direction. After the second rotation member 107 moves to the reference position, the holding member 152 stops at the initial position.

The convex 112 releases the fit in the concave 202 as in the first embodiment, or separates from the upper plane of the rotation member 201.

As described above, the ultrasound probe according to this embodiment can facilitate lock of the rotation member by the operator with a simpler configuration than the first embodiment. The simpler configuration makes it possible to manufacture the fixing part at lower cost and more easily than in the first embodiment.

Third Embodiment

Next, an ultrasound probe according to a third embodiment will be described. The entire configuration of the ultrasound probe according to this embodiment is similar to that of the first embodiment. The ultrasound probe according to this embodiment is different from the ultrasound probes according to the first and second embodiments in that the horizontal-bend knob is fixed with a magnetic force. Hereinafter a configuration of locking the rotation member with magnetic a force will be described.

A fixing part according to this embodiment has an axial tube member piercing the center of the rotation axis of the rotation member, and a fixing member fixed to the axial tube member.

The rotation member is configured so as to rotate around the axial tube member in a direction orthogonal to the axial tube member.

Moreover, the rotation member is fixed with respect to a rotation along the axial tube member.

The fixing member is fixed with respect to both the direction along the axial tube member and the direction orthogonal to the axial tube member. Moreover, the fixing member is placed at a position near the rotation member.

A magnet is attached to a plane of the rotation member facing the fixing member.

A coil is placed on a plane of the fixing member facing the rotation member. This coil is placed so as to be at a position facing the magnet of the rotation member when the bending part 022 is not bent rightward or leftward and the tip part 023 is not tilted rightward or leftward.

The fixing member is provided with a power source for generating electric current. Moreover, the fixing member is provided with a switch for causing the power source to generate electric current.

When the operator turns on the switch, electric current is generated by the power source and sent to the coil. When electric current is sent from the power source to the coil, a magnetic field is generated at the coil.

When a magnetic field is generated at the coil of the fixing member, an attraction force acts between the coil and the magnet of the rotation member, and locks the rotation member, whereby the rotation member is inhibited from rotating. At this moment, the coil is placed so as to be at the position facing the magnet of the rotation member in a state that the bending part 022 is not bent rightward or leftward and the tip part 023 is not tilted rightward or leftward. Therefore, the rotation member is locked without the tip part 023 tilted rightward or leftward.

As described above, the ultrasound probe according to this embodiment can lock the horizontal-bend knob 013 by magnetic force when there is no bend rightward or leftward. Consequently, it is possible to create, with a simple configuration, a mechanism for locking the horizontal-bend knob 013 only when there is no rightward or leftward bend.

The invention claimed is:

1. An ultrasound probe, comprising:
a rod-like tip part configured to penetrate into a body cavity;
an ultrasound emitting part placed at the tip part to emit ultrasonic waves to a subject;
a first bending part configured to bend the tip part in a direction substantially orthogonal to the emission direction; and
a fixing part configured to, when the first bending part is not bending the tip part toward any side of the direction orthogonal to the emission direction, lock the first bending part and inhibit the first bending part from bending the tip part in the direction substantially orthogonal to the emission direction;
the first bending part includes:
a rotation member rotatable around an axis; and
two wires, whose one ends are connected to the rotation member at positions facing across a center of the axis, respectively, and whose other ends are fixed to the tip part at positions facing across a center of the tip part in the direction substantially orthogonal to the emission direction, respectively; and
the fixing part includes a fixing member placed at a position fixed with respect to a rotation direction of the rotation member;

one of the rotation member and the fixing member includes a concave, and the other includes a convex; and in a state that the first bending part is not bending the tip part toward any side of the direction orthogonal to the emission direction, the fixing part locks the rotation member by fit of the concave and the convex;

wherein the rotation member is provided with a concave and the fixing member is provided with a convex, the ultrasound probe further comprising:

a first elastic member configured to press the fixing member from the rotation member side, wherein the fixing part includes a lock mechanism disposed to a rear side of the fixing member opposite to a plane with the convex disposed so as to be movable in the direction orthogonal to the rotation direction, the lock mechanism being configured to compress the elastic member when pressed to stop and lock the rotation member in a state that the convex and the concave fit each other, and configured to release the stop by a next press to separate the convex from the concave by a force of the elastic member and release the lock of the rotation member;

and further comprising:

an axial tube member piercing through the center of the axis of the rotation member to fix the fixing member with respect to the rotation direction, wherein:

the lock mechanism includes:
 a second rotation member in contact with the fixing member to rotate around the axial tube member;
 a pressing member placed so as to fit into a rear plane of the second rotation member opposite to a plane in contact with the fixing member; and
 a holder member fixed to the axial tube member to cover the pressing member and the second rotation member;

the second rotation member and the pressing member each include a protrusion on a plane parallel to the axial tube direction in contact with the holder member;

the holder member includes shallow grooves and deep grooves disposed along the axial tube direction, alternately in the rotation direction, on a plane parallel to the axial tube direction in contact with the pressing member and the second rotation member;

the protrusion of the pressing member is to be housed into the deep groove; and the second rotation member rotates around the axial tube member by friction when pressed, and the protrusion of the second rotation member is housed into the next groove of the holder member.

2. An ultrasound probe, comprising:

a rod-like tip part configured to penetrate into a body cavity;

an ultrasound emitting part placed at the tip part to emit ultrasonic waves to a subject;

a first bending part configured to bend the tip part in a direction substantially orthogonal to the emission direction; and a fixing part configured to, when the first bending part is not bending the tip part toward any side of the direction orthogonal to the emission direction, lock the first bending part and inhibit the first bending part from bending the tip part in the direction substantially orthogonal to the emission direction;

the first bending part includes:
 a rotation member rotatable around an axis; and
 two wires, whose one ends are connected to the rotation member at positions facing across a center of the axis, respectively, and whose other ends are fixed to the tip part at positions facing across a center of the tip part in the direction substantially orthogonal to the emission direction, respectively; and the fixing part includes a fixing member placed at a position fixed with respect to a rotation direction of the rotation member;

one of the rotation member and the fixing member includes a concave, and the other includes a convex;

in a state that the first bending part is not bending the tip part toward any side of the direction orthogonal to the emission direction, the fixing part locks the rotation member by fit of the concave and the convex;

a protruding direction of the convex disposed to one of the fixing member and the rotation member and an opening direction of the concave disposed to the other are directions orthogonal to the rotation direction;

the convex and the concave are positioned facing each other when the first bending part is not bending the tip part;

the fixing member is capable of moving close to and away from the rotation member; and the convex fits into the concave when the fixing member moves close to the rotation member;

wherein the rotation member includes a concave and the fixing member includes a convex, the ultrasound probe further comprising:

a first elastic member configured to press the fixing member from the rotation member side, wherein the fixing part includes a lock mechanism disposed to a rear side of the fixing member opposite to a plane with the convex disposed so as to be movable in the direction orthogonal to the rotation direction, the lock mechanism being configured to compress the elastic member when pressed to stop and lock the rotation member in a state that the convex and the concave fit each other, and configured to release the stop by a next press to separate the convex from the concave by a force of the elastic member and release the lock of the rotation member;

and further comprising:

an axial tube member piercing through the center of the axis of the rotation member to fix the fixing member with respect to the rotation direction, wherein:

the lock mechanism includes:
 a second rotation member in contact with the fixing member to rotate around the axial tube member;
 a pressing member placed so as to fit into a rear plane of the second rotation member opposite to a plane in contact with the fixing member; and
 a holder member fixed to the axial tube member to cover the pressing member and the second rotation member;

the second rotation member and the pressing member each include a protrusion on a plane parallel to the axial tube direction in contact with the holder member;

the holder member includes shallow grooves and deep grooves disposed along the axial tube direction, alternately in the rotation direction, on a plane parallel to the axial tube direction in contact with the pressing member and the second rotation member;

the protrusion of the pressing member is to be housed into the deep groove; and the second rotation member rotates around the axial tube member by friction when pressed, and the protrusion of the second rotation member is housed into the next groove of the holder member.

3. The ultrasound probe according to claim 1, wherein:
the fitting planes of the second rotation member and the pressing member facing each other are planes of a triangular corrugated shape;
the protrusion of the second rotation member is formed by making part of the plane of the triangular corrugated shape protrude outside from a periphery of the second rotation member, the part of the plane of the triangular corrugated shape having a slope deeply cut in toward the pressing member with respect to the rotation direction;
an edge of the groove of the holder member closer to the second rotation member tilts in a same direction as the protrusion of the second rotation member; and
the second rotation member rotates by friction of the triangular corrugated planes, the protrusion of the second rotation member and the tilt of the groove of the holder member.

4. The ultrasound probe according to claim 2, wherein:
the fitting planes of the second rotation member and the pressing member facing each other are planes of a triangular corrugated shape;
the protrusion of the second rotation member is formed by making part of the plane of the triangular corrugated shape protrude outside from a periphery of the second rotation member, the part of the plane of the triangular corrugated shape having a slope deeply cut in toward the pressing member with respect to the rotation direction;
an edge of the groove of the holder member closer to the second rotation member tilts in a same direction as the protrusion of the second rotation member; and
the second rotation member rotates by friction of the triangular corrugated planes, the protrusion of the second rotation member and the tilt of the groove of the holder member.

5. The ultrasound probe according to claim 3, wherein the second rotation member rotates by friction of the triangular corrugated planes when the second rotation member travels toward the fixing member along the axial tube member and the protrusion comes out of the groove, and rotates by friction of the protrusion of the second rotation member and the tilt of the groove of the holder member when the second rotation member travels toward the pressing member along the axial tube member.

6. The ultrasound probe according to claim 4, wherein the second rotation member rotates by friction of the triangular corrugated planes when the second rotation member travels toward the fixing member along the axial tube member and the protrusion comes out of the groove, and rotates by friction of the protrusion of the second rotation member and the tilt of the groove of the holder member when the second rotation member travels toward the pressing member along the axial tube member.

7. The ultrasound probe according to claim 5, further comprising a knock member fixed with the pressing member across the holder member to press the pressing member toward the fixing member.

8. The ultrasound probe according to claim 6, further comprising a knock member fixed with the pressing member across the holder member to press the pressing member toward the fixing member.

9. The ultrasound probe according to claim 7, wherein:
the convex of the fixing member is formed like a rod; and
the fixing member includes:
a second elastic member configured to press the convex toward the rotation member; and
a holding member configured to hold the convex and the second elastic member.

10. The ultrasound probe according to claim 8, wherein:
the convex of the fixing member is formed like a rod; and
the fixing member includes:
a second elastic member configured to press the convex toward the rotation member; and
a holding member configured to hold the convex and the second elastic member.

* * * * *